US005101816A

United States Patent [19]

Wilcox

[11] Patent Number: 5,101,816

[45] Date of Patent: Apr. 7, 1992

[54] SEPARABLE VALVE ASSEMBLY

[75] Inventor: Orland W. Wilcox, Pasadena, Calif.

[73] Assignee: Gentex Corporation, Pomona, Calif.

[21] Appl. No.: 537,456

[22] Filed: Jun. 5, 1990

[51] Int. Cl.[5] .............................. A61M 15/00

[52] U.S. Cl. .............................. 128/200.24; 128/202.27; 128/205.24

[58] Field of Search .............................. 128/201.19, 202.27, 128/201.24, 205.24, 205.25, 200.24

[56] References Cited

U.S. PATENT DOCUMENTS

| | | | |
|---|---|---|---|
| 1,615,718 | 1/1927 | Olgard | 128/205.24 |
| 1,630,209 | 5/1927 | Olgard | 128/205.24 |
| 2,684,066 | 7/1954 | Glidden | 128/205.24 |
| 2,868,198 | 1/1959 | Brooke | 128/205.24 |
| 2,953,129 | 9/1960 | Bloom et al. | 128/201.19 |
| 3,348,537 | 10/1967 | Miller et al. | 128/201.19 |
| 4,616,646 | 10/1986 | Beaussant | 128/205.24 |
| 4,648,394 | 3/1987 | Wise | 128/201.24 |
| 4,756,308 | 7/1988 | Ryback | 128/201.19 |

*Primary Examiner*—Edgar S. Burr
*Assistant Examiner*—Aaron J. Lewis
*Attorney, Agent, or Firm*—Donald D. Mon

[57] ABSTRACT

A valve assembly for use in breathing apparatus which is made in two sub-assemblies to facilitate repair at low cost. One assembly is adapted to be detachably mounted to a face mask and carries modules for communication accessories. A second subassembly is threadedly attached to the first sub-assembly and carries the valving members necessary to admit air or breathable gases to the face mask and to allow the escape of exhaled gases. The second sub-assembly valve portion is made in two sections which can be disassembled for repair with readily replacable valving elements for easy maintenance.

3 Claims, 3 Drawing Sheets

SEPARABLE VALVE ASSEMBLY

FIELD OF THE INVENTION

This invention relates to breathing masks, and especially to a readily serviceable mask.

BACKGROUND OF THE INVENTION

Valve assemblies for use with breathing masks have been of unitary construction demanding that the valve be removed from the mask or the whole mask discarded when the valve became inoperable. It is an object of this invention to provide an adapter for a separable valve assembly that will be structurally sound for use in breathing apparatus to provide the regulated intake and exhalation of breathable gas mixtures or air.

A further object is to provide for easy disassembly of the two piece valve from the adapter to provide for the adapter portion attached to a face mask to remain in position.

Another object of the invention is to provide an adapter with integrated components to carry auxiliary communication circuits.

Yet another object of the invention is to provide an adapter that is easily detachable from said valve assembly, and said valve assembly can carry replaceable valving elements to provide easy repair of the valve in case of malfunction or wear.

The adapter assembly of this invention can adapt the well-known United States Air Force combination valve, MIL-V-27296 to the well-known U.S. Air Force Folding, Hanging, Quick Don Mask which carries a part number 358-1002 in the U.S. Air Force Inventory of parts. The adapter will accept valves manufactured by any qualified source according to the military specification.

An advantage feature of the invention is that the adapter assembly can accept standard microphone attachments such as are made to microphone part numbers M-169 or M-101 in the United States Air Force inventory.

BRIEF DESCRIPTION OF THE INVENTION

The preferred embodiment of the invention is an adapter assembly provided with a tubular body adapted to be inserted into a matching internal cylindrical recess in a well-know standard face mask. Quick engagement bayonet pin engagement means for secure attachment to the face mask and an attachment block for communication means is fixed to the tubular mask engagement portion of the adapter. Internal thread means are provided ar the end opposite to the tubular body and on the same axial alignment to provide for assembly with a standard valve. Sealing means and lock screws are provided to seal between the valve assembly and the adapter assembly to lock the adapter and valve together.

DESCRIPTION OF THE INVENTION

Figure 1:
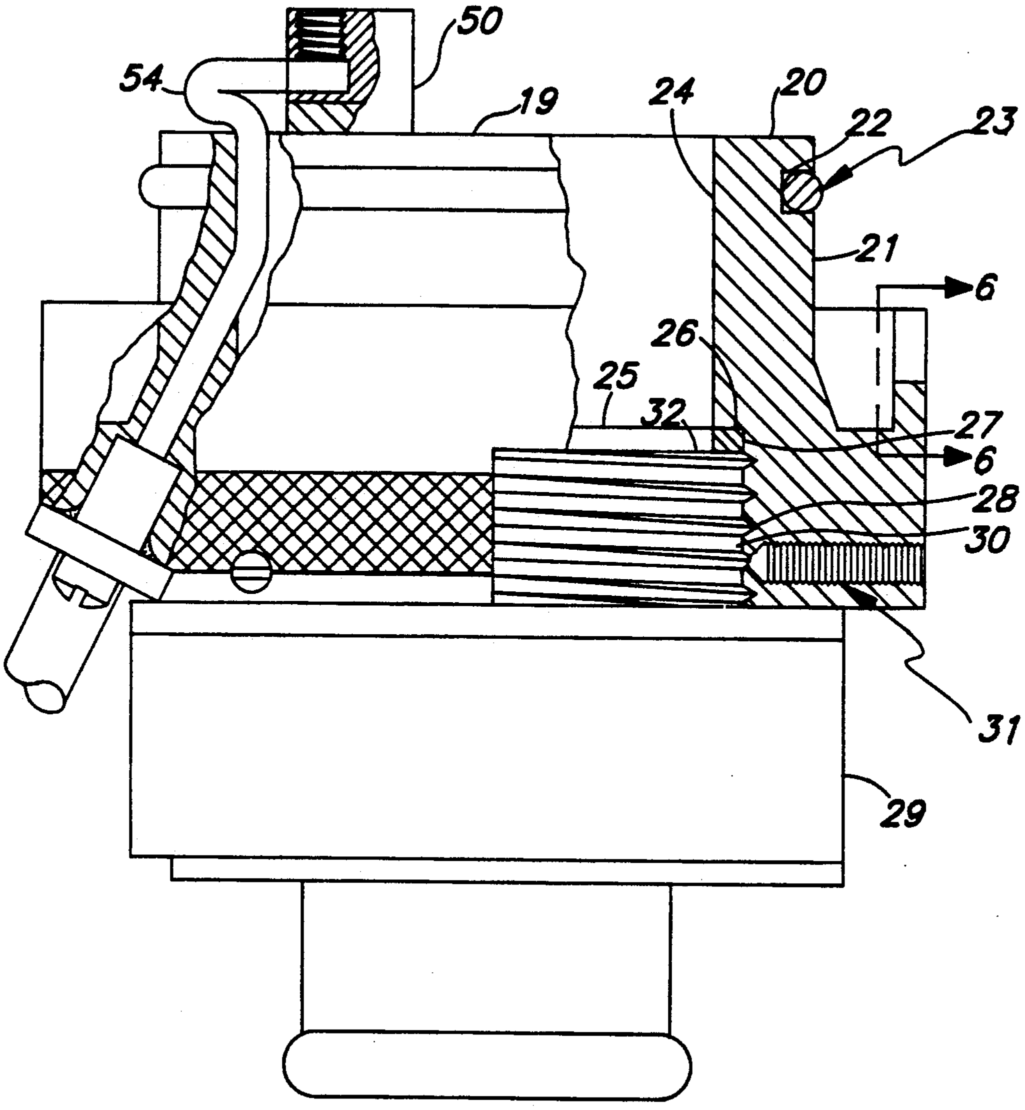
FIG. 1 is a front view of the presently preferred embodiment of the invention partially in cross-section in assembly with a standard valve.

The presently preferred embodiment of the invention is shown in FIG. 1.

An adapter 19 with tubular nose member 20 is adapted with a cylindrical surface 21 that is provided with a groove 22 adapted to receive an O ring 23 for sealable attachment to a Quick Don Face Mask of well-known design. An internal cylindrical bore 24 provides free flow of the breathable gas mixture, primarily air. An internal groove 25 provides a sealing face 26 for seating a silicone gasket 27. An internal thread 28 provides for threadable attachment of a valve body 29 that can be seen in FIG. 1.

In FIG. 1 is shown the valve body 29 threadably engaged to the embodiment of the adapter 19 in FIG. 1 with outside thread 30. Three set screws exemplified by 31 are threadable engaged through adapter 19 to lock against external thread 30 of the valve body. A portion of the thread 30 and the end surface 32 of the valve body 29 engages the sealing gasket 27 to provide for containment of the flow of the breathable gas into the face mask.

Figure 4:
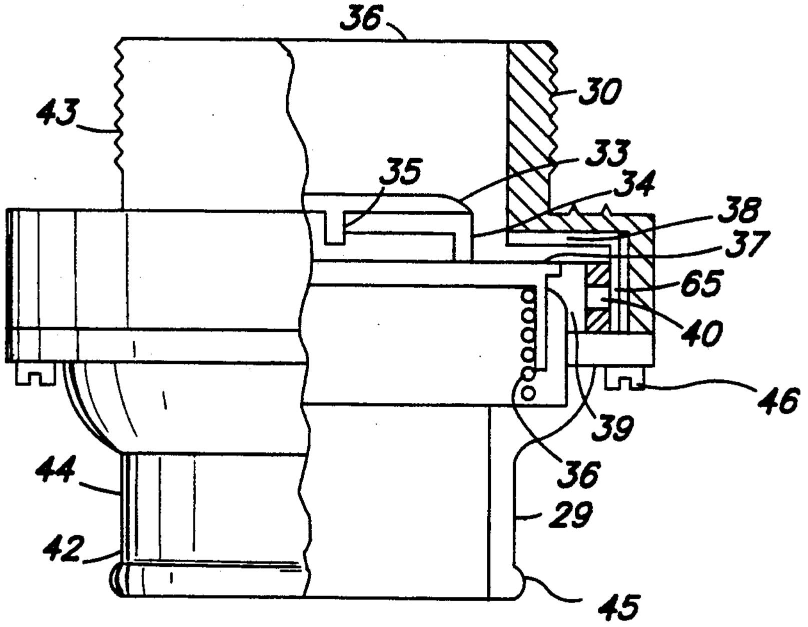
FIG. 4 is a front view, partially in cross-section of the valve portion of FIG. 1.

FIG. 4 shows an embodiment of the standard valve 29 partially in cross-section to show its adaptation for breathable gas or air flow and for attachment to the adapter 19. The external thread 30 is adapted to threadably engage with the adapter member 19 that is the embodiment of this invention. A flapper valve 33 is engaged with a member 34 through a central pin 35 with forced fit to allow the breathable gas to flow through passage 36 to the adapter 19 and thence on into the Quick Don Breathing Mask.

Figure 5:
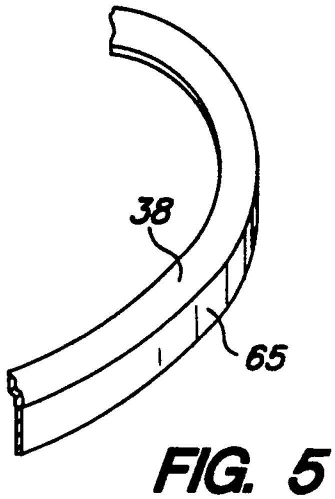
FIG. 5 is a fragment of an oblique view of a member shown in FIG. 4.

Member 34 is biased by spring member 36 so that its upper surface 37 may seal against leaf valve member 38. When exhaled gases travel through the adapter 19 into the central bore 36 of the valve assembly the pressure causes body 34 to move downward against the spring bias 86 to permit exhaust gases to flow through the passage 39 and the radial passages 40 to the leaf type valving elements 65 as shown in FIG. 5 permitting the exhaust of the expelled breathable gas.

For convenience in assembly the valve is constructed with two body elements, an air supply attachment element 42 and an adapter attachment element 43.

Figure 2:
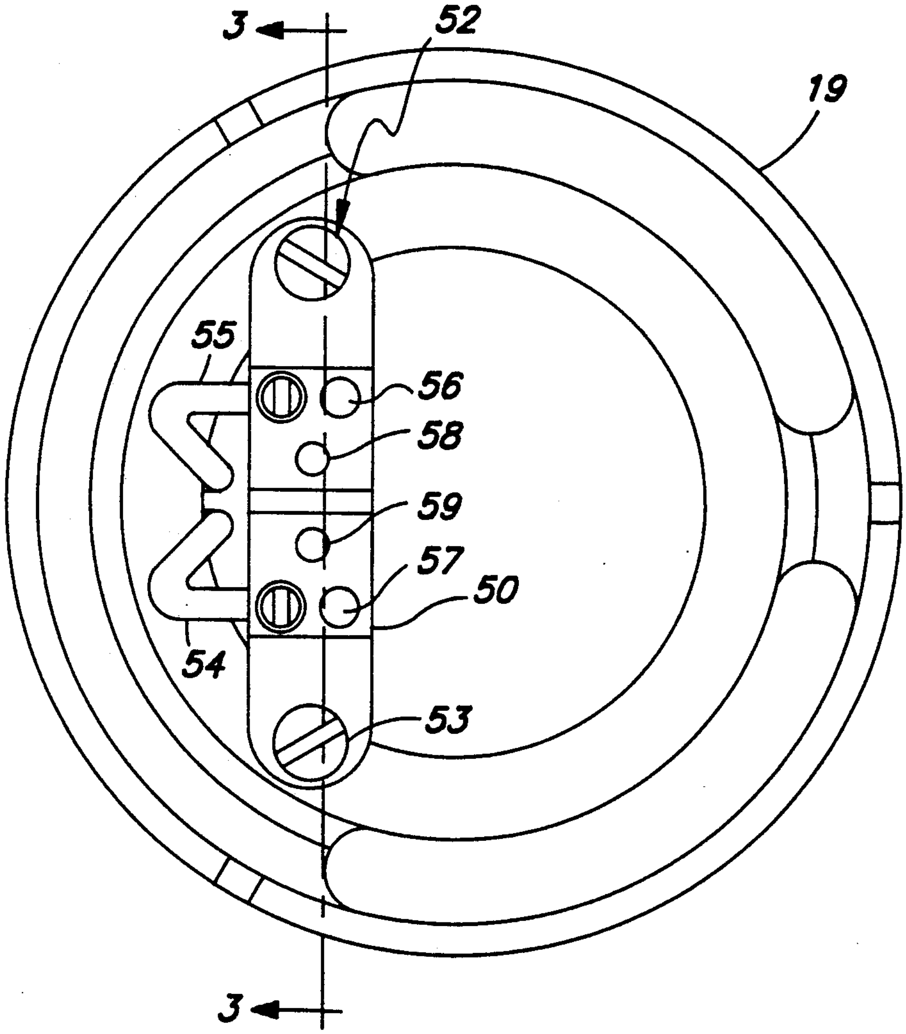
FIG. 2 is a top view of the embodiment of the invention shown in FIG. 1.
Figure 3:
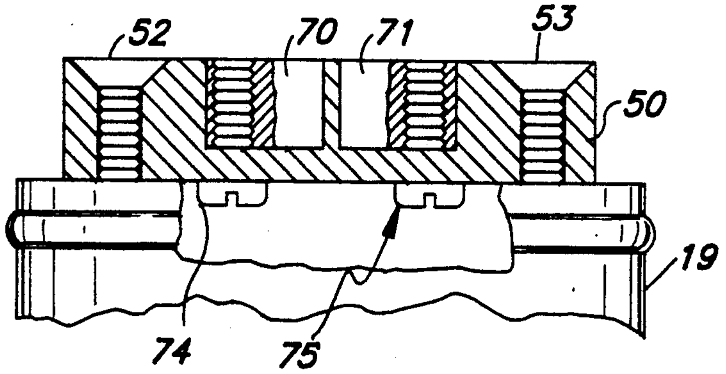
FIG. 3 is a cross-section of FIG. 2 shown on line 3—3.

The air supply attachment element 42 has a tubular nose 44 and an annular raised boss 45 which provides for attachment to a breathable gas or air supply. The two parts of valve assembly 9 are held together by screws 46. The position of the separable assembly of the valve permits rapid, convenient repair or replacement of the flapper valve 33, the leaf valves 38, and other portions of the valve assembly that may be damaged by wear or other effects. This is made possible by the disassembly of the valve by means of its thread 30 attachment to the valve adapter assembly 19 that is the embodiment of this invention. In addition to the advantages of the adapter combined with the valve assembly, the adapter also carries a microphone mounting block 50 as can be seen in FIGS. 1, 2, and 3 adapted to be mounted to the valve adapter 19 with screws 52 and 53. The block 50 would preferably be made of an electrically insulative material and conductor blocks 70 and 71 attached to mounting block 50 by screws 74 and 75 would carry the communication leads. Wires 54 and 55 are adapted to lead to a cable attachment assembly of standard design for attachment to a communications source. Receptacles 56 and 57 provide for wire leads to a standard microphone in a face mask and pin receptacles 58 and 59 provide for plugging-in of a microphone assembly that is conventionally found in a Quick Don Face Mask. The microphone adapter block 50 is therefore suited for many types of standard microphones.

Figure 6:
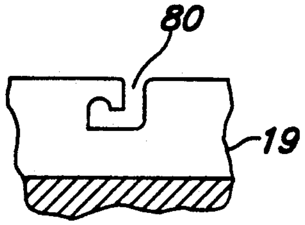
FIG. 6 is a fragmentary view taken on line 6—6 of FIG. 1.

In FIG. 6 is shown a typical bayonet type engagement slot 80 as is used on the adapter 19 to engage with standard bayonet attachment pins on the face masks, hereinbefore referenced by the specification number, for secure attachment by a partial turn of the adapter to the breathable face mask.

This invention is not to be limited by the embodiment shown in the drawings and described in the description, which is given by way of example and not of limitation but only in accordance with the scope of the appended claims.

I claim:

1. Adapter means adapted for use between a breathing face mask and a valve means, said adapter means comprising:

an adapter member, said adapter member having a first and a second end, said first end provided with tubular connector means, said tubular connector means provided with sealing means, said sealing means being adapted to seal between said adapter member and a face mask;

said second end of said adapter means having internal screw thread means, said screw means having a coincident axis with said tubular connector means, said internal screw thread means being adapted threadably to attach a valve means to said adapter;

sealing gasket means, said sealing gasket means being adapted to seal said valve means to said adapter member for passage of breathable gas, whereby separating said thread means, enables said valve means to be repaired;

locking means between said adapter means and said valve means;

twist lock means adapted to secure said adapter means to said face mask means; and communication adapter block means, said communications adapter block means being provided with wire receptacle means and plug receptacle means adapted for connection to a communication system, and being adapted to remain assembled with the adapter means when said valve means is separated from it.

2. Breathing valve means adapted for use with breathing face mask means, comprising:

adapter means, said adapter means adapted to engage said breathing valve means.

said breathing valve means having inlet flapper valve means and outlet leaf valve means adapted for inhalation and exhalation of breathable gas to a breathing face mask, said breathing valve means being adapted readily to be detachable from said adapter means for repair; and communication block means, said communication block means adapted to be mounted on said adapter means, said communication block means being adapted to remain with said adapter means when said breathing valve means is separated from said adapter means.

3. Breathing valve means according to claim 2 in which said breathing valve means has a first and a second member, said first member adapted to assemble with said face mask adapter means, second member adapted to hold said inlet flapper valve means and said outlet leaf valve means in assembly with said first member, said second member being adapted to engage a source of breathable gas, and said second member being detachable from said first member for repair of said valve means.

* * * * *